United States Patent [19]
Wasserman et al.

[11] Patent Number: 5,735,805
[45] Date of Patent: Apr. 7, 1998

[54] FOOT ORTHOSIS WITH DETACHABLE SOLE PLATE

[75] Inventors: Constance V. Wasserman, Palm Harbor, Fla.; Harold T. Varn, Lawrenceville, Ga.; Clarence E. Hess, Safety Harbor, Fla.

[73] Assignee: Restorative Care of America Incorporated, Clearwater, Fla.

[21] Appl. No.: 807,886

[22] Filed: Feb. 26, 1997

[51] Int. Cl.⁶ ................................................ A61F 5/00
[52] U.S. Cl. .................. 602/10; 602/11; 602/27; 36/15
[58] Field of Search .................. 602/10–12, 23, 602/27, 28, 29; 36/103, 110, 12, 15, 23, 62, 65, 66

[56] References Cited

U.S. PATENT DOCUMENTS

| | | |
|---|---|---|
| 3,416,518 | 12/1968 | Samuels et al. |
| 3,494,355 | 2/1970 | Wolpow ............................ 602/10 |
| 3,735,758 | 5/1973 | Novotney |
| 3,735,759 | 5/1973 | MacKay |
| 3,802,424 | 4/1974 | Newell |
| 3,878,626 | 4/1975 | Isman |
| 4,223,456 | 9/1980 | Cohen |
| 4,289,122 | 9/1981 | Mason et al. |
| 4,505,269 | 3/1985 | Davies et al. ........................ 602/27 |
| 4,572,169 | 2/1986 | Mauldin et al. ....................... 602/27 |
| 4,887,369 | 12/1989 | Bailey et al. |
| 4,962,760 | 10/1990 | Jones ................................. 602/27 |
| 4,974,344 | 12/1990 | Ching |
| 4,974,583 | 12/1990 | Freitas ............................. 602/27 X |
| 5,052,128 | 10/1991 | Lonardo |
| 5,088,479 | 2/1992 | Detoro |
| 5,154,695 | 10/1992 | Farris et al. |
| 5,176,624 | 1/1993 | Kuehnreich |
| 5,298,013 | 3/1994 | Lonardo |
| 5,317,822 | 6/1994 | Johnson |
| 5,368,551 | 11/1994 | Zuckerman ....................... 602/27 X |
| 5,372,576 | 12/1994 | Hicks ............................... 602/27 |
| 5,433,695 | 7/1995 | Drennan ........................... 602/10 |
| 5,460,600 | 10/1995 | Bieling ............................ 602/27 |
| 5,545,127 | 8/1996 | DeToro ............................ 602/27 |
| 5,569,173 | 10/1996 | Varn |
| 5,569,174 | 10/1996 | Varn |
| 5,593,383 | 1/1997 | DeToro ............................ 602/27 |
| 5,620,411 | 4/1997 | Schumann et al. ................. 602/27 X |

*Primary Examiner*—Linda C. Dvorak
*Attorney, Agent, or Firm*—Zarley, McKee, Thomte, Voorhees, & Sease

[57] ABSTRACT

A conventional foot orthosis has a stiff L-shaped splint including a substantially horizontal foot portion with a lower surface. A fabric anklet is on the foot orthosis and has a bottom surface extending over the bottom surface of the splint. An attachment screw is rotatably mounted on the foot portion of the splint and has an enlarged diameter head extending downwardly through an opening in the bottom surface of the anklet. An elongated toe plate has an aperture therein which communicates with a forwardly extending elongated slot. A planar sole plate is rigidly secured to a lower surface of the toe plate and has an aperture therein communicating with a rearwardly extending elongated slot. The apertures are adapted to register with each other to permit the head of the attachment screw to extend through the apertures. A surface connection element detachably secures the toe plate to the bottom surface of the anklet when the sole plate has been moved so that the screw moves into the elongated slot of the toe plate.

3 Claims, 4 Drawing Sheets

FOOT ORTHOSIS WITH DETACHABLE SOLE PLATE

BACKGROUND OF THE INVENTION

L-shaped foot orthoses are commonly used on predominantly bedfast patients to protect the patient's heel from bed sores and to correct for foot drop wherein the patient's foot moves away from a substantial right angle position with respect to the patient's leg. These devices sometimes have sole plates secured to the bottoms thereof to engage the floor at such times as the patient is walking or being moved from place to place. In order to prevent the sole plate from contaminating the bed of the patient, the sole plate is often detachably secured to the bottom surface of the orthosis so that it can be removed when the patient moves from a walking mode back to a resting position in the patient's bed.

Existing detachable sole plates for such orthoses sometimes require tools in order to be attached to or removed from the orthoses.

It is therefore a principal object of this invention to provide a detachable sole plate for a foot orthosis which is easy to remove from the orthosis, or to be placed on the orthosis without the use of tools.

It is a further object of this invention to provide a sole plate for an orthosis which can be quickly and easily attached to the orthosis or removed therefrom.

These and other objects will be apparent to those skilled in the art.

SUMMARY OF THE INVENTION

A conventional foot orthosis has a stiff L-shaped splint including a substantially horizontal foot portion with a lower surface. A fabric anklet is on the foot orthosis and has a bottom surface extending over the bottom surface of the splint. An attachment screw is rotatably mounted on the foot portion of the splint and has an enlarged diameter head extending downwardly through an opening in the bottom surface of the anklet.

An elongated toe plate has an aperture therein which communicates with a forwardly extending elongated slot. A planar sole plate is rigidly secured to a lower surface of the toe plate and has an aperture therein communicating with a rearwardly extending elongated slot. The apertures are adapted to register with each other to permit the head of the attachment screw to extend through the apertures. A surface connection element detachably secures the toe plate to the bottom surface of the anklet when the sole plate has been moved so that the screw moves into the elongated slot of the toe plate.

DESCRIPTION OF THE PREFERRED EMBODIMENT

Figure 1:
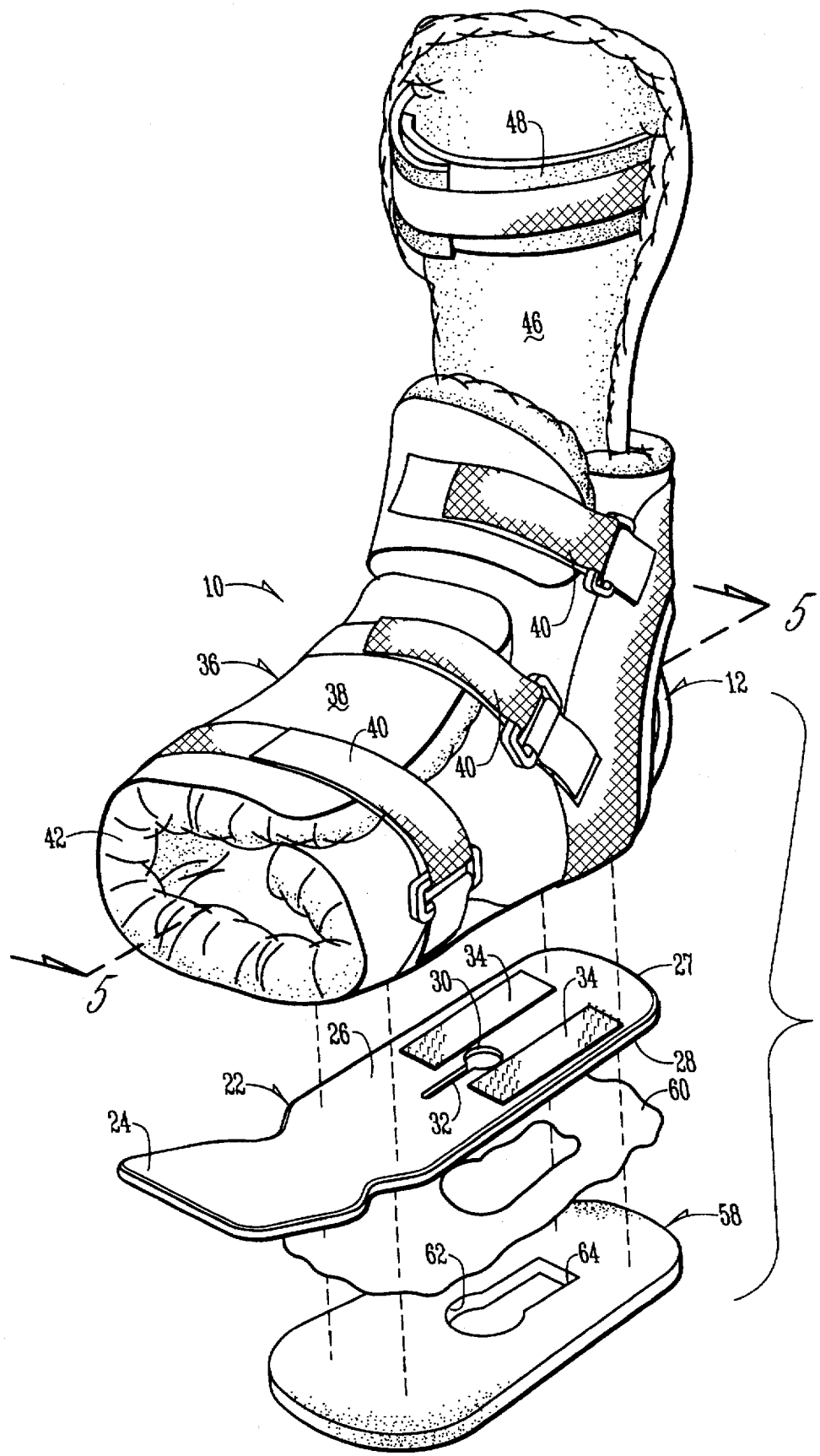
FIG. 1 is an exploded perspective view of the device of this invention.

The orthosis 10 of the invention has a plastic splint 12 which is substantially stiff but which has some slight resiliency. Splint 12 has a leg portion 14, an enlarged heel portion 16, a foot portion 18, and a bottom surface 20 (FIG. 5).

Figure 5:
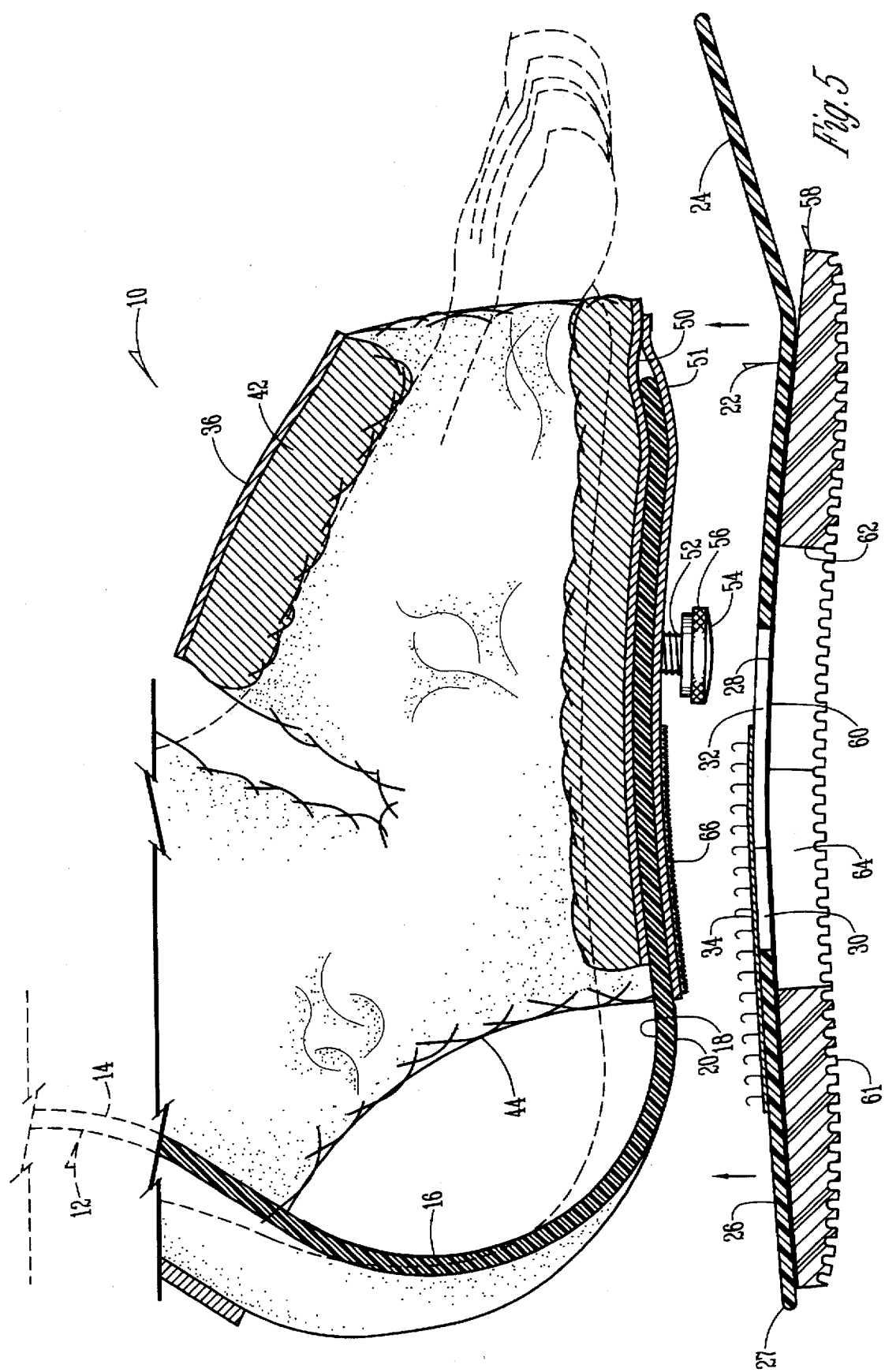
FIG. 5 is an enlarged scale sectional view taken on line 5—5 of FIG. 1.

A toe plate 22 (FIG. 1) has an inclined toe support surface 24 on its forward end, a planar upper portion 26, a rearward end 27 (FIG. 1) and a lower surface 28 (FIG. 5). An aperture 30 is centrally located in planar portion 26 and is connected to a longitudinally extended elongated slot 32. The slot extends forwardly from aperture 30 as shown in FIG. 1. A pair of hook surface securing attachment bands 34 are mounted on the planar surface 26 on opposite sides of aperture 30 as best shown in FIG. 1. The members 34 are secured by glue or the like to the upper planar surface 26.

An anklet 36 (FIG. 1) has a top portion 38, a plurality of straps 40, foot padding 42, an open heel portion 44, and a leg pad 46 secured in place by strap 48. Anklet 36 has a pocket 50 in its lower portion (FIG. 5) and a lower surface 51.

An attachment screw 52 extends vertically downwardly from splint 12 and is rotatably secured to the splint and is adapted to rotate about the axis of the screw. The lower end of the screw has a circular head 54 rigidly secured thereto. The head 54 has a knurled rim 56 extending around the periphery thereof.

A sole plate 58 of rubber or the like is secured by glue layer 60 to the bottom side of toe plate 22. Sole plate 58 has a textured lower surface 61. An aperture 62 of a diameter greater than the aperture 30 in toe plate 22 is located in sole plate 58. Aperture 62 is connected to an elongated longitudinal slot 64 which extends rearwardly from aperture 62. Slot 64 has a width substantially greater than the slot 32. Slot 32 has a width substantially equal to the diameter of attachment screw 52. Sole plate 58 is arched slightly upwardly at its midpoint with respect to its opposite ends as best shown in FIG. 5.

As seen in FIG. 5, a pair of elongated attachment loop surface bands 66 are secured to the bottom surface 51 of anklet 36 and are adapted to engage the attachment bands 34 on the top surface of toe plate 22 as will be described hereafter.

Figure 2:
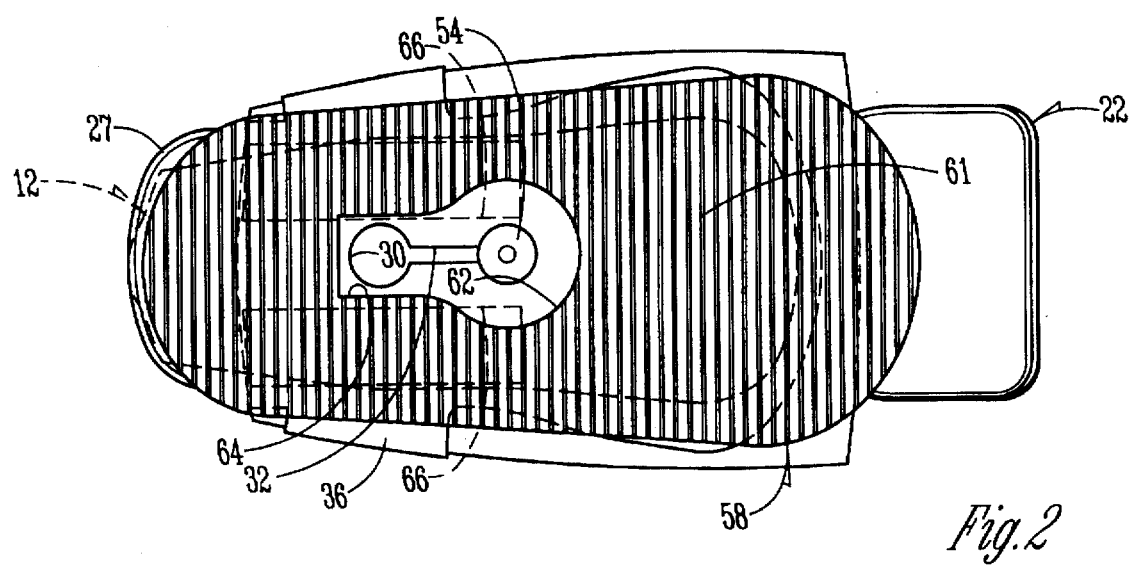
FIG. 2 is a bottom plan view shown at a smaller scale of the assembled device of FIG. 1.
Figure 3:
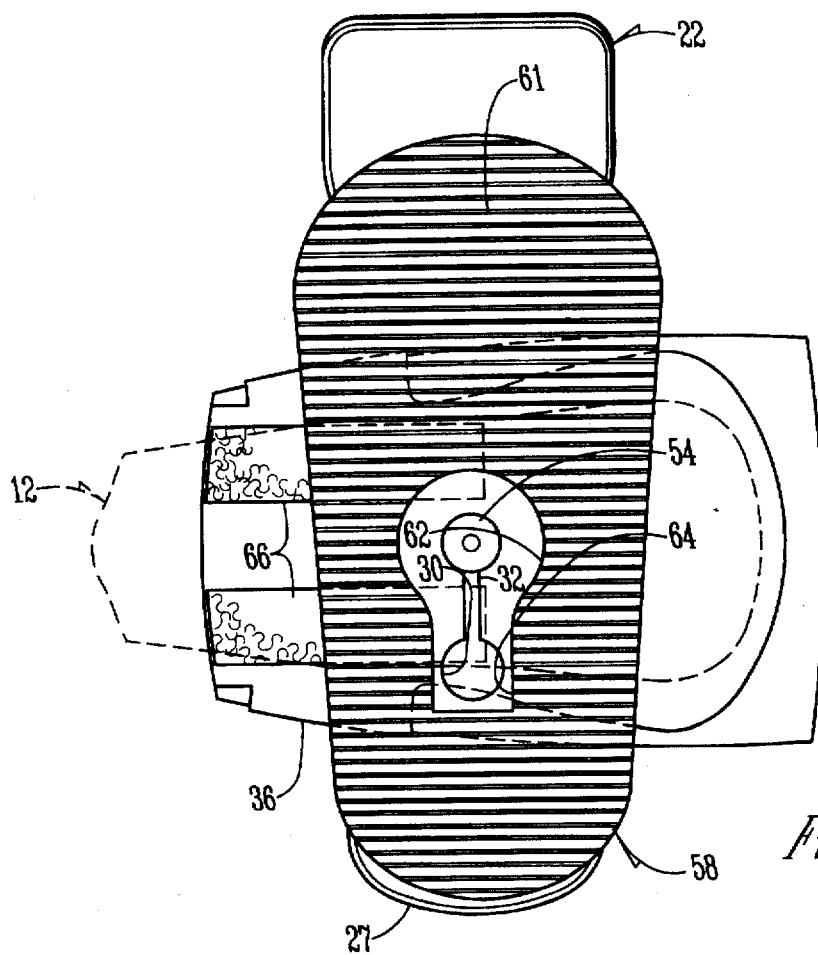
FIG. 3 is a bottom plan view of the device in a stage when the sole plate is either being removed or attached to the orthosis.
Figure 4:
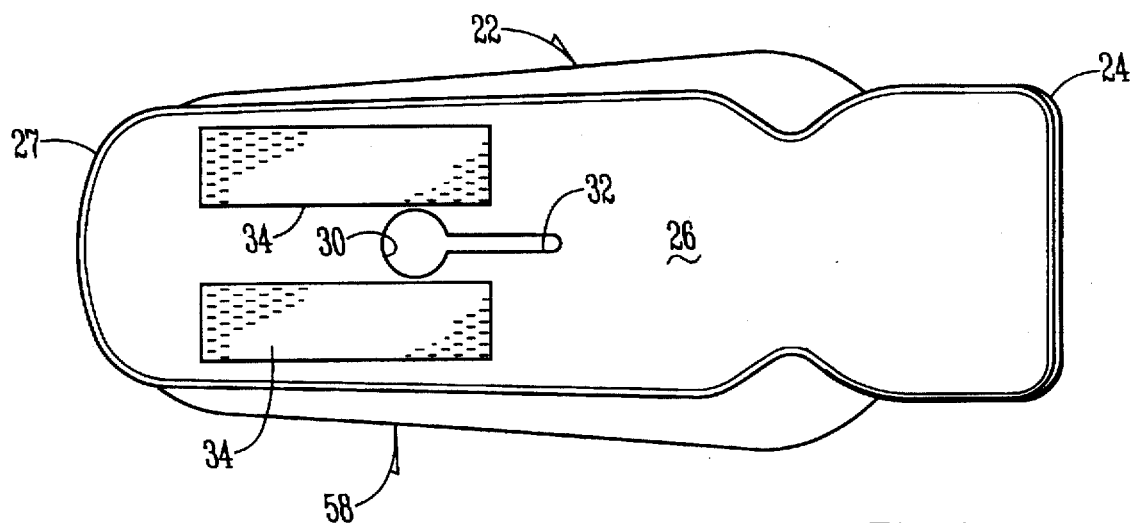
FIG. 4 is a top plan view of the toe post and sole plate secured to each other.

When it is desired to attach the assembled structure of the sole plate 58 and toe plate 22 to the bottom of anklet 36, the sole plate 58 with attached toe plate 20 is oriented at right angles with respect to anklet 36 wherein the head 54 on attachment screw 52 extends through the aperture 30 in the toe plate and into the slot 64 in the sole plate. By applying a slight amount of pressure on the sole plate in a direction towards the anklet, the head 54 on the attachment screw extends completely through aperture 30 and slot 64. The sole plate 58 with attached toe plate is then slidably moved to the forward end of slot 32 (FIG. 3) and rotated about attachment screw 52 in a clockwise direction as viewed in FIG. 3 to the position of FIG. 2 wherein the longitudinal axes of the toe plate and the sole plate are in alignment with the longitudinal axes of the anklet. If necessary, the screw 62 can be finger tightened against the bottom surface of toe plate 22 to better insure the interlocking relationship therebetween.

After the patient has completed the walking exercise, the toe plate and the sole plate can be removed by reversing the above steps. It should be noted that when the components are in the position shown in FIG. 2, the attachment band 34 on the top of toe plate 22 will engage the attachment bands 66 on the bottom of anklet 36 to releasably bond the toe plate to the bottom of the anklet.

It is therefore seen that the sole plate 58 can be easily attached to or removed from the otherwise assembled orthosis 10 for the intended purpose, and this can be quickly and easily done without the use of tools. It is therefore seen that this invention will achieve at least all of its stated objectives.

What is claimed is:

1. An ambulatory attachment for a foot orthosis having a stiff L-shaped splint including a substantially horizontal foot portion having a lower surface, an anklet on said foot orthosis having a bottom surface extending over the bottom surface of said splint, and an attachment screw rotatably mounted on said foot portion of said splint and having an enlarged diameter head and extending downwardly through an opening on the bottom surface of said anklet, comprising, an elongated toe plate having an aperture therein communicating with a forwardly extending elongated slot, a planar sole plate rigidly secured to a lower surface of said toe plate and having an aperture therein communicating with a rearwardly extending elongated slot, whereupon the head of said attachment screw can be inserted through the aperture in said toe plate and said attachment screw can be slidably moved to the end of said forwardly extending slot dwelling within the aperture in said sole plate, and a surface connection means detachably securing said toe plate to the bottom surface of said anklet when said sole plate has been moved so that said screw moves into the elongated slot of said toe plate.

2. The device of claim 1 wherein the aperture in said sole plate is larger than the aperture in said toe plate.

3. The device of claim 2 wherein the elongated slot in said sole plate is wider than the elongated slot in said toe plate.

* * * * *

UNITED STATES PATENT AND TRADEMARK OFFICE
CERTIFICATE OF CORRECTION

PATENT NO. : 5,735,805
DATED : April 7, 1998
INVENTOR(S) : Constance V. Wassermann, Harold T. Varn, and Clarence E. Hess It is certified that error appears in the above-identified patent and that said Letters Patent is hereby corrected as shown below:

Cover page, item [75],

Correct the first inventor's last name to read as follows:

- Wassermann -.

Column 3, lines 10 through 15 should be printed as follows:

an elongated toe plate having an aperture therein communicating with a forwardly extending elongated slot, a planar sole plate rigidly secured to a lower surface of said toe plate and having an aperture therein communicating with a rearwardly extending elongated slot, whereupon Signed and Sealed this Twenty-second Day of September, 1998

Attest:

BRUCE LEHMAN

Attesting Officer

Commissioner of Patents and Trademarks